United States Patent [19]

Galleymore et al.

[11] 4,298,730
[45] Nov. 3, 1981

[54] PROCESS FOR THE PRODUCTION OF A SURFACTANT CONTAINING SUCROSE ESTERS

[75] Inventors: Harry R. Galleymore, Bath; Kenneth James, Reading; Haydn F. Jones, Reading; Chaman L. Bhardwaj, Reading, all of England; James S. Plant, deceased, late of Reading, England; by Aline P. Plant, administrator, Manchester, England

[73] Assignee: Talres Development (N.A.) N.V., Curacao, Netherlands Antilles

[21] Appl. No.: 174,277

[22] Filed: Jul. 31, 1980

[30] Foreign Application Priority Data

Dec. 19, 1979 [GB] United Kingdom ............... 43762/79
May 1, 1980 [GB] United Kingdom ............... 14370/80

[51] Int. Cl.$^3$ .................. C07H 13/06; C11D 1/66; C11D 9/26; C11D 11/04
[52] U.S. Cl. .................... 536/119; 252/89.1; 252/132; 252/174.17; 260/410.6
[58] Field of Search ............ 252/89.1, 132, 174.21, 252/174.17; 260/410.6; 536/119

[56] References Cited

U.S. PATENT DOCUMENTS

| | | | |
|---|---|---|---|
| 2,970,962 | 2/1961 | Hass | 252/135 |
| 3,251,827 | 5/1966 | Schnell | 536/119 |
| 3,480,616 | 11/1969 | Osipow | 536/119 |
| 3,558,597 | 1/1971 | Von Brachel | 536/119 |
| 3,714,144 | 1/1973 | Feuge | 536/119 |
| 3,792,041 | 2/1974 | Yamagishi | 536/119 |
| 3,867,301 | 2/1975 | Watanabe | 252/132 |
| 3,963,699 | 6/1976 | Rizzi | 534/119 |
| 3,996,206 | 12/1976 | Parker | 536/119 |
| 4,032,702 | 6/1977 | James | 536/119 |

FOREIGN PATENT DOCUMENTS

1399053 6/1975 United Kingdom ............... 536/119

*Primary Examiner*—Dennis L. Albrecht
*Attorney, Agent, or Firm*—Ostrolenk, Faber, Gerb & Soffen

[57] ABSTRACT

The process for the preparation of a surfactant mixture containing sucrose mono- and di-esters, by reacting a starting mixture including solid particulate sucrose, at least one triglyceride of a fatty acid having at least 8 carbon atoms and a basic transesterification catalyst, at a temperature of from 110° to 140° C. at atmospheric pressure and in the absence of any solvent, is improved by using a starting mixture which:

(a) contains a di and/or mono-glyceride in an amount to provide a hydroxyl value of greater than 500 mg KOH/100g of starting mixture;

(b) contains at least 10% by weight of a fatty acid soap in addition to the basic transesterification catalyst, at least 50% by weight of the soap being potassium soap, and (c) (when the soap content is less than 20% by weight) contains at least 25% by weight of sucrose.

The improved process gives good yields in much shorter reaction times and the products have high HLB values.

20 Claims, 10 Drawing Figures

PROCESS FOR THE PRODUCTION OF A SURFACTANT CONTAINING SUCROSE ESTERS

This invention relates to the production of a surface active material comprising or consisting of one or more fatty acid esters of sucrose.

Esters of sucrose with fatty acids, particularly the sucrose mono-esters and di-esters, are potentially very valuable as surfactants and have a number of unique advantages in this role. Thus, they are non-toxic, odourless and tasteless; they are non-irritating to the skin; and, when ingested, they hydrolyse to form normal food products. Unlike most surfactants, they are biodegradable under both aerobic and anaerobic conditions; and, unlike most other non-ionic surfactants, they are solid and thus readily usable in powdered or spray-dried products. They are very good emulsifiers; and they perform well as detergents, either alone or in combination with anionic surfactants, and can be formulated either as high-foaming or low-foaming detergents. Accordingly, they can be used generally as domestic or industrial detergents, and also in specialised uses such as additives for foodstuffs, animal feeds, cosmetics, pharmaceuticals and agricultural chemicals.

However, in spite of possessing these advantages, sucrose ester surfactants have never been exploited to their full potential, because of difficulties arising in their production. Many processes have been proposed for the preparation of sucrose ester surfactants but, due to technical and economical disadvantages, it is still not easy to achieve large-scale industrial production at a price competitive with other surfactants.

Sucrose esters cannot efficiently be prepared by the direct esterification of sucrose with a fatty acid, but three other methods are possible: reaction with a fatty acid chloride; reaction with a fatty acid anhydride; and transesterification with a fatty acid ester. The reaction with acid chlorides, which is performed in the presence of pyridine, is uneconomical and will not give good yields of sucrose monoesters or diesters: it can be used to prepare sucrose octa-esters, but these are unsatisfactory as surfactants. Acid anhydrides of the higher fatty acids are not available commercially, and their preparation is complicated and expensive. Consequently, attempts at finding a commercial process for the preparation of sucrose ester surfactants have concentrated on the transesterification reaction, generally using methyl or glyceryl esters of fatty acids.

Most of the known transesterification processes are carried out in a solvent. The most commonly used solvent is dimethylformamide. The reaction is usually performed at about 90° C., in the presence of an alkaline catalyst (e.g. potassium carbonate), using the methyl ester of the fatty acid. It is necessary to remove all traces of water, by heating the system under reduced pressure as each component is added; and the methanol, or other alkanol, by-product of the transesterification must also be removed by prolonged heating of the reaction mixture under reduced pressure, so as to drive the reaction equilibrium in the desired direction. The critical need for anhydrous conditions, the prolonged heating under reduced pressure and, above all, the use of a solvent such as dimethylformamide are all serious disadvantages of this process: not only must the dimethylformamide be recovered for economic operation, but its residual presence can render the product toxic and smelly.

U.S. Pat. No. 3,480,616 (of Osipow et al) describes a modified form of the solvent transesterification process in which sucrose is reacted with a methyl ester, such as methyl tallowate, in a solvent such as propylene glycol which dissolves the sucrose but not the fatty component. An emulsifying agent is used, and the reaction is performed in a so-called "micro-emulsion". Although this process avoids the disadvantages arising from the use of a toxic solvent such as dimethylformamide, it still has to be performed under reduced pressure and in the absence of any water.

A later modification of the solvent transesterification process, described in British Pat. No. 1,332,190 (of Dai-Ichi Kogyo Seiyaku Co. Ltd.) uses water as the solvent. The sucrose is completely dissolved in water in the presence of a fatty acid soap, a fatty acid ester and a transesterification catalyst are added, and the mixture is dehydrated under reduced pressure and at elevated temperature so as to produce a homogeneous melt. The melt is then maintained at elevated temperature, for the transesterification reaction to take place. Although this process avoids the problems which arise when using an organic solvent such as dimethylformamide or propylene glycol, it is a multistage process which still requires heating under reduced pressure, and the pressure must be carefully controlled in relation to the temperature when producing the dehydrated melt, in order to avoid hydrolysis of the fatty acid ester. The process is, therefore, undesirably complicated for use on an industrial scale.

A solvent-free transesterification process has also been proposed in J. Amer. Oil Chem. Soc. 1970, 47, (2), 56–60; and U.S. Pat. No. 3,714,144 (of Feuge et al). In accordance with this process, it is stated that the solvent-free transesterification must be carried out with the sucrose in the molten state; and the process is, therefore, performed at a temperature of from 170° to 190° C. After a short time, the molten sucrose begins to degrade to a black tarry mass, and the reaction with the fatty acid ester must necessarily be performed very quickly: the reaction is generally stopped within 20 minutes, and sometimes after only 2 minutes. As in the solvent processes, the reaction is performed under reduced pressure, to distil off the alcoholic by-product. Furthermore, the reaction must be performed in the presence of an alkali-free anhydrous soap, which serves to solubilise the fatty acid ester in the molten sucrose and to catalyse the transesterification: alkoxides, free alkalis and ordinary soaps are entirely unsatisfactory as catalysts in this process, and their presence results in very rapid decomposition of the sucrose and darkening of the reaction mixture. Thus, although this process avoids some of the disadvantages arising from the use of a solvent such as dimethylformamide, it has disadvantages of its own tending to make it unsatisfactory as a commercial-scale preparation for sucrose ester surfactants. Specifically, it is difficult to control, because the reaction must be completed very quickly to avoid degrading the sucrose, it must still be performed under reduced pressure, and it requires the use of expensive special catalysts.

U.S. Pat. No. 3,558,597 (of von Brachel) describes a process in which sucrose and a fatty acid methyl ester are transesterified in the presence of a basic catalyst under conditions chosen to distil off the alcohol by-product. Those conditions require a reduced pressure, typically about 15 mmHg. Similarly, U.S. Pat. No. 3,963,699 (of Rizzi and Taylor) describes the transesterification of a fatty acid methyl ester with sucrose, in a process for the production of higher esters of sucrose, again under reduced pressure. In the former process, the only additive to the reaction mixture apart from the sugar and methyl ester is the transesterification catalyst, potassium carbonate. The reaction takes at least 8 hours. In the latter process, the reaction is effected in the presence of a catalyst (sodium hydride or potassium metal) and about 9 or 10% by weight of an alkali metal soap. Esterification takes 2 hours.

U.K. Pat. No. 1,399,053 (of Tate & Lyle Ltd.) describes a process in which a surfactant is prepared by reacting solid particulate sucrose with at least one triglyceride in the presence of a basic transesterification catalyst, at a temperature in the range of from 110° C. to 140° C., at atmospheric pressure and in the absence of any solvent. In this process, it is recommended that a so-called "emulsifier" for the solid sugar and liquid triglyceride is incorporated in the reaction mixture, typically at a level of about 5 to 10% by weight. The emulsifier preferred in that patent is the crude surfactant mixture obtained by that process, although mixed glycerides can also be used. Soaps are not recommended. This process produces a surfactant material containing sucrose esters together with soap, glycerides and some sugar and can be used as an effective surfactant in its own right. The product typically has an HLB value of about 10 or 11. The reaction proceeds in two clearly defined stages, the first of which is an "initiation" stage and the second is a transesterification stage. The two stages together take 8 hours or more.

We have now surprisingly found that, if a potassium fatty acid soap is incorporated into the starting mixture at a relatively high level, a product can be obtained which contains a similar amount of sucrose esters, but which can, in many cases, have a higher HLB value, and which is obtained in a very much shorter time.

A conventional transesterification reaction with basic catalysis yields a fairly high proportion of soap in the product, typically between 20 and 30% by weight. We have now found that incorporation of substantial amounts of soap in the starting mixture yields a product without a corresponding substantial increase in soap, although the soap level is raised to a certain extent. Most surprisingly, addition of significant levels of soap to the starting material has been found to produce a dramatic reduction in the reaction time, in many cases completely obviating the initiation period. According to this process, surfactant material can be obtained which contains the same amount of sucrose esters as the conventional process of British Pat. No. 1,399,053, but in as little as one-quarter of the time.

According to the present invention there is provided a process for the preparation of a surfactant mixture containing sucrose mono- and di- esters, by reacting a starting mixture including solid particulate sucrose, at least one triglyceride of a fatty acid having at least 8 carbon atoms and a basic transesterification catalyst, at a temperature of from 110° to 140° C. at atmospheric pressure and in the absence of any solvent, characterised in that the starting mixture:

(a) contains a di- and/or mono- glyceride in an amount to provide a hydroxyl value of greater than 500 mg KOH/100 g of starting mixture;

(b) contains at least 10% by weight of a fatty acid soap in addition to the basic transesterification catalyst, at least 50% by weight of the soap being potassium soap; and (c) (when the soap content is less than 20% by weight) contains at least 25% by weight of sucrose.

The hydroxyl value referred to here is the concentration (estimated by titration) of hydroxyl groups in the total glyceride component (feedstock), calculated in mgKOH/100 g of total starting mixture. Thus, for example, a starting mixture containing triglyceride, sucrose and soap has a hydroxyl value of zero since there are no free hydroxy groups in the glyceride feedstock. A combination of mono-, di- and triglycerides gives various hydroxyl values. The method used for determining hydroxyl value is given in "Test Methods For Fatty Acids", AFAO, 1968.

The term "starting mixture" used herein means the complete mixture of reactants at the start of the sucrose esterification. It thus includes sucrose, soap, catalyst and glycerides, but does not include any alkali metal hydroxide added earlier to form soap (see passage below with regard to pre-forming soap).

The optimum soap concentration in the starting mixture is about 25 to 30% by weight, this level producing as high a level of sucrose ester in the product as any in a convenient reaction time. Higher initial soap levels can be used, but the higher the soap content the more viscous the reaction mixture becomes, and levels much above 30% can lead to problems with stirring. Lower soap levels are also less desirable and the starting mixture preferably contains at least 15%, more preferably at least 17.5%, and even more preferably at least 20% by weight of soap.

It is an essential feature of the present invention that the soap incorporated is mainly or completely a potassium soap of a fatty acid. The effect produced by the potassium soap is not shown by other alkali metal soaps. Thus, for example, sodium soaps lead to the production, in the same time, of a very much reduced yield of sucrose esters. In view of this, the soap incorporated in the starting mixture must be comprised of at least 50% by weight of potassium soap, and ideally should consist entirely of potassium soap. The soap should preferably be comprised of at least 60%, more preferably at least 70%, of potassium soap. The potassium soap may be a potassium soap of any long chain fatty acid and in general should contain an acid moiety with at least 8 carbon atoms. The fatty acid moiety may be saturated or unsaturated and conveniently comprises a mixture of fatty acids derived from a naturally occurring glyceride or a modified (e.g. hydrogenated) glyceride.

The soap used in the starting mixture may be incorporated as a ready-formed component, especially when the fatty acid moiety of the soap is required to be different from that of the glyceride in the starting mixture. Where, however, the two fatty moieties may be the same, it is possible to form at least part of the soap in situ, e.g. by reaction of the triglyceride with potassium hydroxide, before addition of the sugar and catalyst. This will, of course, add somewhat to the reaction time, but the saponification reaction under these conditions is very rapid and enough soap may be generated in one hour or less. The sucrose should not be added until the generation of the soap is substantially complete.

The fatty acid moiety of the soap may comprise the same fatty acids as in the triglyceride or different ones. Since the soap which remains at the end of the reaction is, in fact, largely the soap initially introduced, the nature of the fatty acid moiety in the soap can be chosen to give a product with particular characteristics, for example hardness, melting point and ease of processing.

Thus, for example, a potassium soap of a fully saturated fatty acid or fatty acid mixture can be incorporated in a transesterification involving a triglyceride of an at least partially unsaturated fatty acid.

One or more triglycerides of fatty acids having from 8 to 22 carbon atoms, preferably at least 12 and most preferably from 16 to 18 carbon atoms, may be used in the process of the invention. It is normally convenient to use naturally occurring mixtures of triglycerides. Both for economic reasons and because it yields a particularly effective surfactant product, the most highly preferred natural triglyceride is tallow, which contains glyceryl esters of stearic, palmitic and oleic acids; but other triglyceride fats and oils can be used, for example lard, palm oil, cottonseed oil, soybean oil, olive oil, groundnut oil, coconut oil, castor oil and linseed oil. However, it is generally less desirable to use triglycerides derived from highly unsaturated fatty acids, for example the so-called "drying oils" such as linseed oil, because they tend to oxidize and become discoloured during the process of the invention and the product has relatively inferior surfactant properties; in general, it is preferred to use triglycerides derived from acids containing not more than one double bond. The presence of hydroxyl groups in the acid chain can also be detrimental to the surfactant properties of the product.

The sucrose used in the process of the invention is normally in the form of particulate refined sugar. The sucrose particle size is not critical, but particles which are too large can be difficult to disperse adequately in the reaction mixture, and it is therefore generally preferred to use sucrose of a particle size smaller than 250 microns.

The equipment used for the reaction may comprise any of the typical components used in this type of process. Efficient stirring is essential and good temperature control is also necessary to avoid local overheating. Exclusion of air and moisture is desirable but not absolutely critical.

The basic catalyst used in the reaction may be any of those conventionally used in such reactions, such as alkali metal carbonates, alkoxides and hydrides. Potassium carbonate, for example, is capable of providing an equilibrium mixture containing up to 18% by weight of sucrose monoester and 8% by weight of sucrose di-ester in a total reaction time of about 6 hours at 125° C.

However, according to a particular feature of this invention, a relatively high yield of sucrose ester can be obtained in a much shorter time using a carbonate catalyst by careful selection of the hydroxyl value of the starting mixture.

In general, we find that the higher the hydroxyl value, up to a maximum of about 7,500, the faster the initial reaction and the quicker an acceptable yield of sucrose ester is obtained. Thus, for example, we have found that tallow can yield a product containing about 25% of sucrose monoester and diester in a reaction at 125° C. in as little as two hours if the hydroxyl value of the glyceride feedstock is adjusted to at least 1,000. In contrast, the yield of sucrose ester under those conditions at a hydroxyl value of zero would be only 2 to 3% after two hours.

Similar reactions using tripalmitin have shown that a product containing 25% of sucrose monoester and diester can be obtained in about 3 hours provided the hydroxyl value of the starting material is adjusted to at least 1,500.

At higher hydroxyl values, the accelerating effect declines and in practice a hydroxyl value for the feedstock of from 1,000 to 7,500 is suitable, especially 1,500 to 5,000.

The desired hydroxyl value of the feedstock can be easily achieved by mixing the required amount of monoglyceride and/or diglyceride with the triglyceride. Conveniently, a mixed glyceride material can be obtained, for example, by interesterification of the triglyceride with glycerol in a solvent and in the presence of a basic catalyst such as potassium carbonate. Such methods are described in detail by Feuge and Bailey, Oil and Soap, 1946, p.259, and Basu and Choudhury, J. Amer. Oil Chem. Soc., 37 (1960), 482. The glyceride mixture obtained can be titrated for hydroxyl value and then used to adjust the hydroxyl value of the feedstock. However, if the soap is to be formed in situ in the feedstock by reaction of the triglyceride with potassium hydroxide, then inevitably mono- and di- glycerides will also be formed at a rate of one free glyceryl hydroxy group per molecule of soap formed. In this situation, the hydroxyl value will correspond to the amount of potassium hydroxide used.

As an alternative to an alkali metal carbonate as basic catalyst, another preferred material is an alkali metal alkoxide, especially the methoxide and glyceroxide. Use of potassium methoxide has been found to yield acceptable levels of sucrose ester in the product in very short times, e.g. in about 30 minutes. With potassium glyceroxide, when the initial soap concentration is about 30%, an equilibrium mixture can be obtained in as little as two hours at 125° C., containing 24 to 25% of sucrose monoester. It will be noted that, where alkoxides are used as the source of catalytic anions, free glyceride hydroxyl groups will be generated by the alkoxide unless there is already a substantial supply of reactive hydroxyl groups in the mixture. Thus, adjustment of the hydroxyl value of the feedstock is less critical when alkoxides are used as the catalysts, since the hydroxyl vallue is to a large extent self-regulating.

As indicated above, the temperature of the reaction should be from 110° C. to 140° C. Naturally, the higher the temperature used, the faster the reaction and the shorter the time required to achieve equilibrium. However, the higher the temperature used, the more discoloration of the sugar occurs and the less acceptable the product becomes. A suitable balance of speed against purity can be achieved working in the range of 120° to 135° C. with a particular preference for 125° to 130° C.

A further advantage of the use of soap in the starting mixture is that the additional viscosity imparted to the glyceride feedstock at the elevated temperatures used helps considerably in maintaining the sucrose in suspension. This means that an even distribution of the sucrose in the reaction mixture can be more easily achieved and this helps to speed the reaction.

The rapid reaction to form sucrose ester in good yield, which can be achieved according to the present invention, means that the process is eminently adaptable for use in a continuous mode. Up until now, sucrose ester production has always been effected batchwise, thus requiring large reaction vessels which are worked intermittently leading to problems of standardisation. Use of potassium soaps in the starting mixture as described above, according to this invention, can mean that fresh starting mixture can constantly be introduce into a through reactor, for example a tubular reactor having an axial stirrer, and the crude product can continuously be removed from the other end.

Selection of the optimum reaction parameters, for example methoxide catalysis or the use of potassium carbonate with a feedstock having a suitably high hydroxyl value, can mean that the residence time of the reaction mixture in the reactor can be as low as two hours. The product obtained can be continuously withdrawn from the reactor, e.g. from the end of a tubular reactor opposite to that into which the reactants are introduced, and further processed. For example, the crude molten surfactant can be cooled and flaked directly, if its hardness is suitable, or can be poured into a solvent system for extraction and/or formation of insoluble alkaline earth metal soaps or Group III metal soaps in the course of purification.

The crude product of the transesterification reaction can itself be used directly as a detergent, in that it contains sucrose esters and soap, together with some sugar. Alternatively, if purified sucrose esters free of soap are required, purification steps such as the treatment with metal salts mentioned above, can be carried out. It might well be supposed that the presence of a high proportion of soap in the starting mixture, as in the process of the invention, would lead to an even higher proportion of soap in the reaction product, and that a high proportion of soap, even the starting mixture concentration, would make it more difficult to obtain a soap-free final product. In fact, as explained earlier, we have found that the final level of soap in the reaction product is only a little higher than the level in the starting mixture. We have also found that soap at a relatively high level in the reaction product is no harder to remove than that at lower levels and can even be easier to remove, for example, if a hard, less-soluble soap is used in conjunction with a glyceride feedstock giving soft, more-soluble sucrose ester products.

The product obtained according to the present invention has a high HLB value which renders it particularly suitable for detergent purposes. A typical product obtained using a feedstock containing 30% by weight of potassium soap is found to contain about 27% by weight of sucrose mono- and di-esters, 15% by weight of sucrose and about 37% by weight of soap, together with only about 18% by weight of mixed glycerides, leading to an HLB value of about 14, which is considerably higher than the 10 to 11 which has been obtained with conventional solvent-free processes. The combination of high soap and low glyceride levels in the product can mean additionally that the material obtained is harder at room temperature and is thus much easier to powder or flake.

According to a further feature of the present invention we have found that the HLB value can be raised even higher, for example to 15, if the feedstock for the reaction, as well as containing relatively high levels of potassium soaps, also contains a higher level of sucrose than is used conventionally. It will readily be realised that, for detergent purposes especially, the higher the HLB value the product has, the better.

In a conventional solvent-free sugar/glyceride transesterification reaction, such as those described in U.K. Pat. No. 1,399,053, as opposed to solvent-based reactions, it is difficult to incorporate sucrose at high levels because of difficulties in suspending the particulate material. In practice, about 27.5% by weight of the reaction mixture was the highest level of sucrose which could easily be reacted. If the sucrose level is maintained at about 30% while the starting mixture includes, say, 30% of soap, then the amount of glyceride in the feedstock is correspondingly decreased. This is the state of affairs generally in the process according to this invention. However, if as well as including a potassium soap at the required level, the starting mixture also includes an increased amount of sucrose, e.g. up to 45 or even 50% by weight of the total, we find that the product contains the same amount of sucrose esters, a slightly lower level of soap and a higher level of sucrose, but, most significantly, a very low level of glycerides. Thus, for example, a starting mixture with an initial composition of 23% glycerides, 45% sucrose and 30% soap and having a hydroxyl value of 1,500, has been found to yield in four hours at 125° C. a product containing 36% soap, 25% sucrose mono- and di-esters, 33% sucrose and only 6% of mono-and di-glycerides and virtually no triglyceride at all. The HLB value of this product is over 15.

One of the problems of increasing the initial sucrose concentration is that it can be difficult to agitate the mixture sufficiently to keep all the sucrose in suspension. As explained above, it appears to be an advantage of the process according to the present invention that the presence of a fairly high proportion of soap in the feedstock causes a higher viscosity which helps to suspend the sucrose, although obviously too high a viscosity can cause problems with stirring unless special measures are employed.

We have also found that the problems of maintaining the sucrose in suspension can largely be solved by recirculating the reaction mixture, e.g. by continuously removing reaction mixture from the bottom of the reactor and ducting it back into the reactor, either at the top or at a lower level so as to provide a constant turnover of the mixture. This can be achieved, for example, by the use of an external recirculation loop of pipework fitted with a recirculation pump.

The pump used in the recirculation loop is preferably a centrifugal pump and should obviously be of a power output suitable for moving the reaction mixture. In a process where soap is formed in situ, the initial molten fatty acid ester and alkali form a relatively mobile liquid but as the soap-forming reaction proceeds and the soap content increases, the melting point of the mix rises and the viscosity rises. After addition of the sugar, the viscosity rises further with some additional soap formation and, of course, sucrose ester formation, but more slowly. In practice, the pump must be able to move a fluid with a viscosity of 100–150 poises. Similarly, the pipework in the recirculation loop must be of a bore and curvature suitable for the transport of such viscous material. A diameter of from 75 to 300 mm is preferred, especially 100 to 200 mm, e.g. about 150 mm.

For convenience, a constant power motor is used, giving a reduction in pumping speed as the viscosity increases. For example, during the initial period of the saponification, when a 2,000 liter reactor contains mainly molten triglyceride, a circulation time of about half a minute can readily be achieved using a pump of about 9.7 Kw (13 h.p.) capacity. This time, however, increases to several minutes as the soap level increases.

In general, the number of total recirculations of the reaction mix should average from 16 to 32, typically about 24, per hour overall.

Alternatively, the recirculation may be effected by internal means, such as a baffle arrangement in the reactor coupled with pumping means. A particular example would be an internal cylindrical housing extending from just below the surface of the reactants to just above the bottom of the reactor, fitted with an internal pump or screw means to lift material inside the cylinder so that it overflows the weir formed by the top of the cylinder and fresh material is drawn in from the bottom of the reactor.

We have found that this kind of recirculation, coupled with efficient low-turbulence stirring in the reactor vessel, gives good bulk mixing of the reactants and enables the sugar content to be increased above previously used levels, thus providing a process for the manufacture of sucrose ester detergent of higher melting point and HLB value.

The following examples illustrate the invention and are described with reference to the accompanying drawings in which:

Each of FIGS. 1, 3, 5 and 7 represents a plot of concentration of sucrose esters and other reaction components against time;

All percentage values are by weight; and the following abbreviations are used:

ME, sucrose monoester; DE, sucrose diester; S, sucrose; MG, monoglyceride; DG, diglyceride; TG, triglyceride.

EXAMPLE 1

Comparison of various initial soap levels

Figure 1:
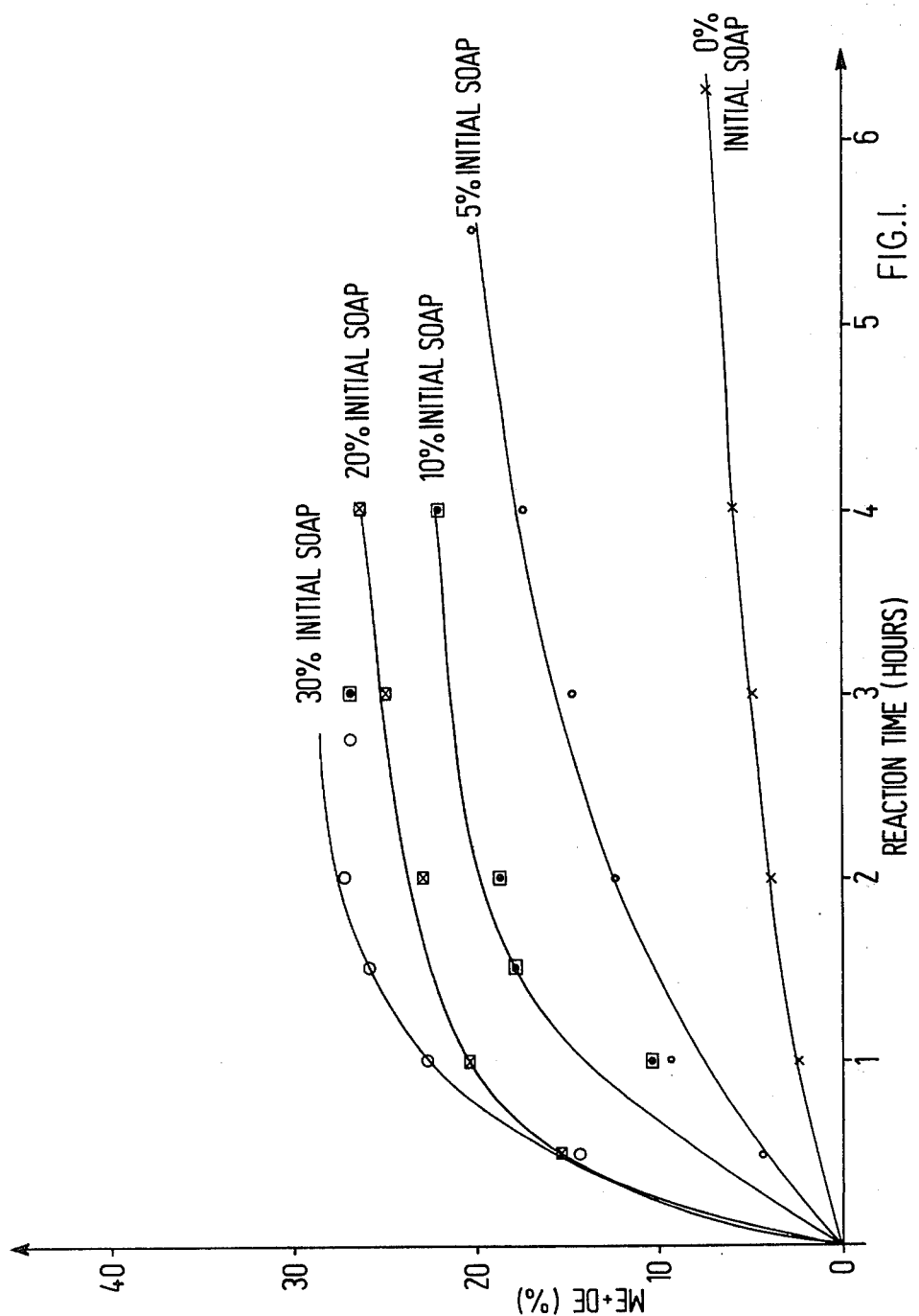
Figure 2:
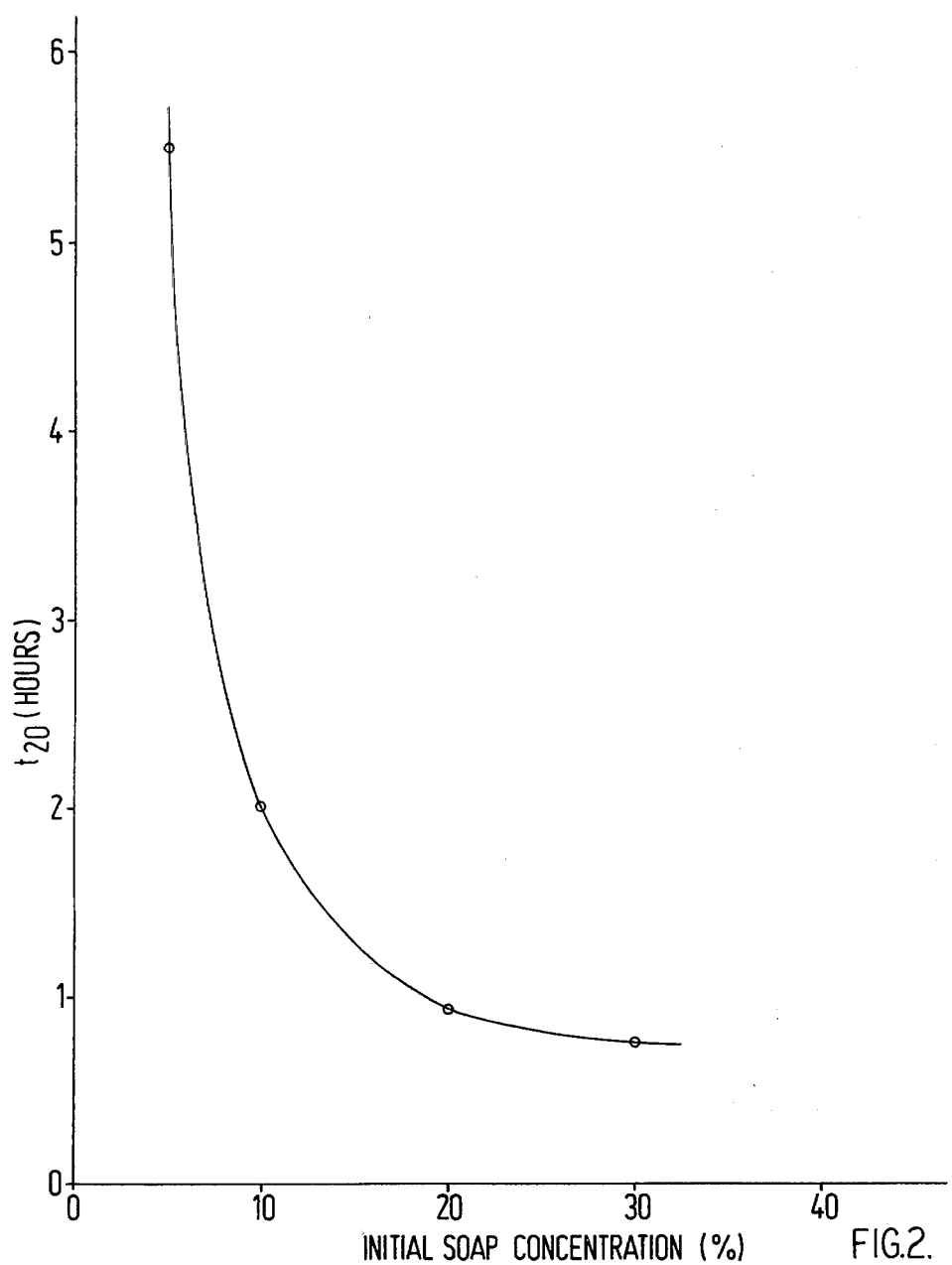
FIG. 2 represents a plot of the time taken to reach a sucrose ester level of 20% against initial soap content.

A series of experiments was carried out using starting mixtures containing increasing amounts of soap but at constant acyl group concentrations. The hydroxyl values and potassium carbonate levels were set so that these components were not rate-limiting. The starting mixtures comprised sucrose (30.0 g), a mixture of mono-, di- and triglycerides (10.0 g), potassium carbonate powder (8.0 g), potassium tallowate (0 g, 5.0 g, 10.0 g, 20.0 g and 30.0 g respectively) and tallow (52.0 g, 47.9 g, 43.8 g, 35.6 g and 27.5 g respectively). The hydroxyl value of the glyceride fraction was initially about 1500 mg KOH/100 g total reactants. Each mixture was stirred at 125° C. under an atmosphere of dried nitrogen and samples were taken at regular time intervals. The samples were analysed by G.L.C. (after silylation using trimethylsilyl chloride and N,N-bis(trimethylsilylacetamide) in a pyridine-chloroform mixture). The results are given in Table 1 and are plotted in FIG. 1 which is a plot of ME+DE against initial soap content. FIG. 2 is a plot of the time taken for the combined sucrose monoester and diester levels to reach 20% ($t_{20}$) against the initial soap content.

TABLE 1

| INITIAL SOAP (%) | | TIME | | | | | | |
|---|---|---|---|---|---|---|---|---|
| | | 30 min | 1h | 1.5h | 2h | 3h | 4h | 5h |
| | | | | | | | | (6h) |
| 0 | KS | | 1.9 | | 2.5 | 5.8 | 7.3 | 8.4 |
| | ME | | 1.5 | | 2.5 | 2.8 | 3.7 | 4.9 |
| | DE | | 1.0* | | 1.5* | 2.1* | 2.5* | 2.7* |
| | ME + DE | | 2.5 | | 4.0 | 4.9 | 6.2 | 7.6 |
| | | | | | | | | (5½h) |
| 5 | KS | 5.0 | 8.3 | | 9.7 | 11.8 | 13.9 | 14.6 |
| | ME | 3.1 | 6.3 | | 8.3 | 9.9 | 11.5 | 11.9 |
| | DE | 1.5* | 3.1* | | 4.1* | 5.0* | 6.0* | 6.0 |
| | ME + DE | 4.6 | 9.4 | | 12.4 | 14.9 | 17.5 | 17.9 |
| 10 | KS | 19.6 | 17.0 | 16.5 | 17.9 | 16.9 | 21.7 | |
| | ME | 5.9 | 6.8 | 10.2 | 10.5 | 15.7 | 12.7 | |
| | DE | 2.1 | 3.6 | 7.8 | 8.3 | 11.4 | 9.3 | |
| | ME + DE | 8.0 | 10.4 | 18.0 | 18.8 | 27.1 | 22.0 | |
| 20 | KS | 27.1 | 27.5 | | 32.3 | 31.5 | 30.7 | |
| | ME | 9.9 | 12.8 | | 14.4 | 16.8 | 17.4 | |
| | DE | 5.6 | 7.8 | | 8.5 | 8.3 | 9.1 | |
| | ME + DE | 15.5 | 20.6 | | 22.9 | 25.1 | 26.5 | |
| | | | | | | (2.45h) | | |
| 30 | KS | 34.4 | 35.2 | 36.6 | 38.1 | 38.1 | 39.4 | 38.6 |
| | ME | 10.0 | 14.5 | 17.0 | 17.9 | 17.4 | 16.3 | 18.2 |
| | DE | 4.5 | 8.3 | 9.0 | 9.4 | 9.3 | 6.9 | 7.2 |
| | ME + DE | 14.5 | 22.8 | 26.0 | 27.3 | 26.7 | 23.2 | 25.9 |

KS = potassium tallowate (%)
ME = sucrose mono-tallowate (%)
DE = sucrose di-tallowate (%)
*sucrose di-tallowate figures so marked are estimated because of interference with tallow at low conversions.

EXAMPLE 2

Comparison of various initial soap levels at constant K+ concentration

Figure 3:
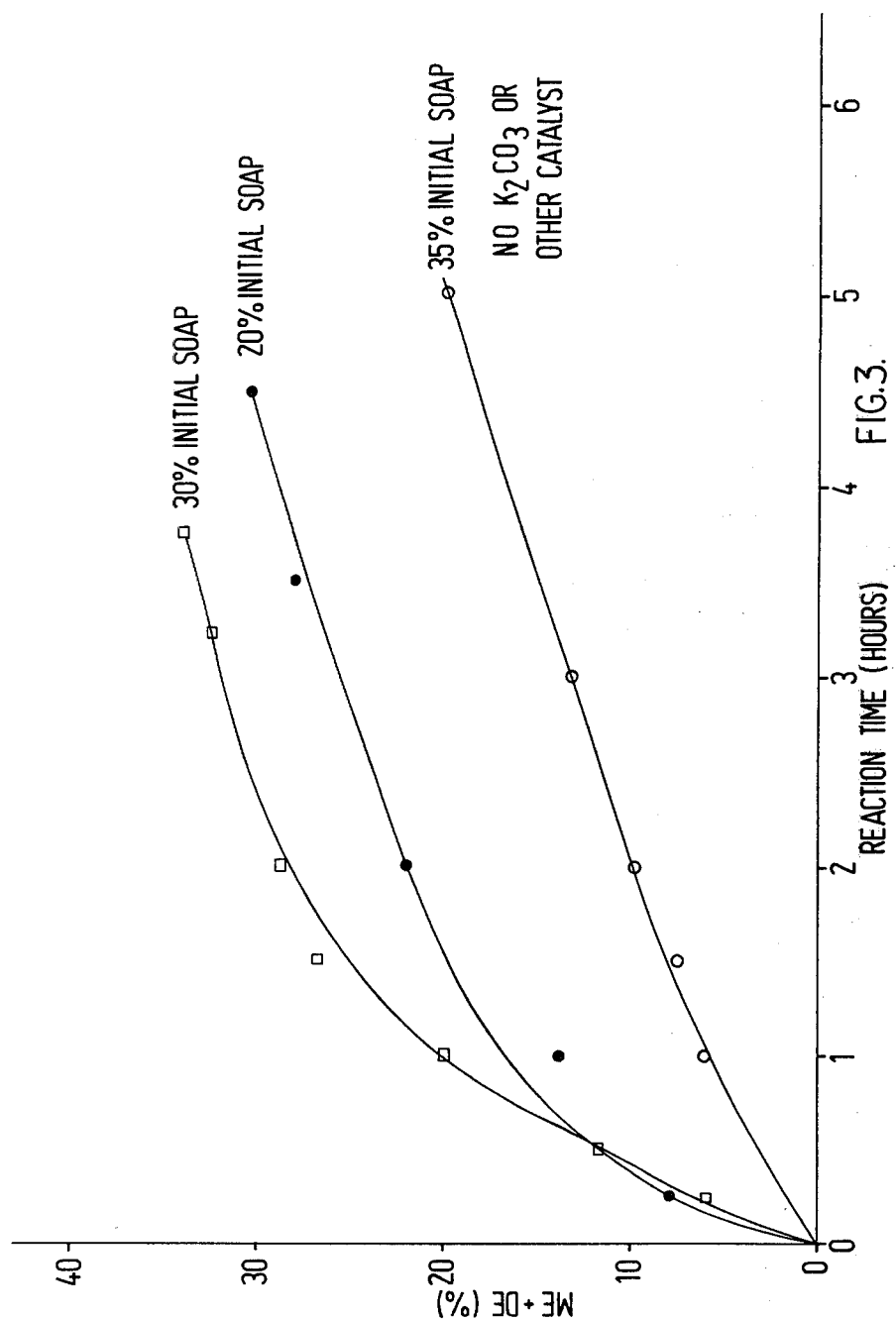

The 20% and 30% initial soap runs of Example 1 were repeated, but adjusting the amounts of potassium carbonate respectively to 4.4 g and 2.5 g. Also, a 35% K soap run was carried out using no potassium carbonate, in order to demonstrate the importance of catalyst as well as soap levels. The results are given in Table 2 and are plotted in FIG. 3.

TABLE 2

| INITIAL SOAP (%) | | TIME | | | | | | |
|---|---|---|---|---|---|---|---|---|
| | | 15 min | 30 min | 1h | 1.5h | 2h | 3h | 4h |
| | | | | | | | | (4.5h) |
| | KS | 22.4 | 28.8 | 24.0 | | 24.1 | 27.5 | 29.6 |
| | ME | 5.8 | 8.3 | 9.8 | | 13.8 | 18.1 | 19.7 |
| 20% | DE | 2.3 | 3.4 | 3.9 | | 8.2 | 10.0 | 10.6 |
| | ME + DE | 8.1 | 11.8 | 13.7 | | 22.0 | 28.1 | 30.3 |
| | KS | 30.8 | 32.3 | 32.9 | 32.3 | 32.6 | 32.4 | 34.0 |
| | ME | 2.8 | 6.7 | 14.4 | 16.7 | 18.8 | 21.7 | 22.8 |
| 30% | DE | 2.8 | 4.7 | 5.5 | 7.9 | 9.9 | 10.5 | 11.0 |
| | ME + DE | 5.6 | 11.4 | 19.9 | 24.6 | 28.7 | 32.2 | 22.8 |
| | | | | | | | | (5hr) |
| | KS | | 35.3 | 35.2 | 35.6 | 35.6 | | 34.4 |
| | ME | | 3.7 | 5.3 | 7.2 | 10.3 | | 15.1 |
| 35% | DE | | 2.3 | 2.3 | 2.6 | 2.9 | | 4.8 |
| (NO K$_2$CO$_3$) | ME + DE | | 6.0 | 7.6 | 9.8 | 13.2 | | 19.9 |

From Examples 1 and 2, it can be seen that increased initial soap levels lead to dramatically decreased times needed to obtain ME+DE in reasonable yields. The run without catalyst shows that both high soap and basic catalyst are required.

EXAMPLE 3

Effect of different alkali metal soaps on equilibrium sucrose ester values

Four different feedstocks were formulated, each containing 30% by weight of sucrose, 38% of mixed glycerides derived from tripalmitin and 30% of stearate soap. The first mixture contained entirely potassium soap, the second a two to one by weight mixture of potassium and sodium soaps, the third a one to two by weight mixture of potassium and sodium soaps and the fourth entirely sodium soaps. The hydroxyl value of each mixture was 1500.

Each mixture was stirred for half an hour at 125° C. and then potassium carbonate (2%) was added and the mixture was vigorously stirred (1200 rpm) for six hours at 125° C. The percentage of sucrose monoester at the end of the six hour reaction period was then measured for each sample.

Figure 4:
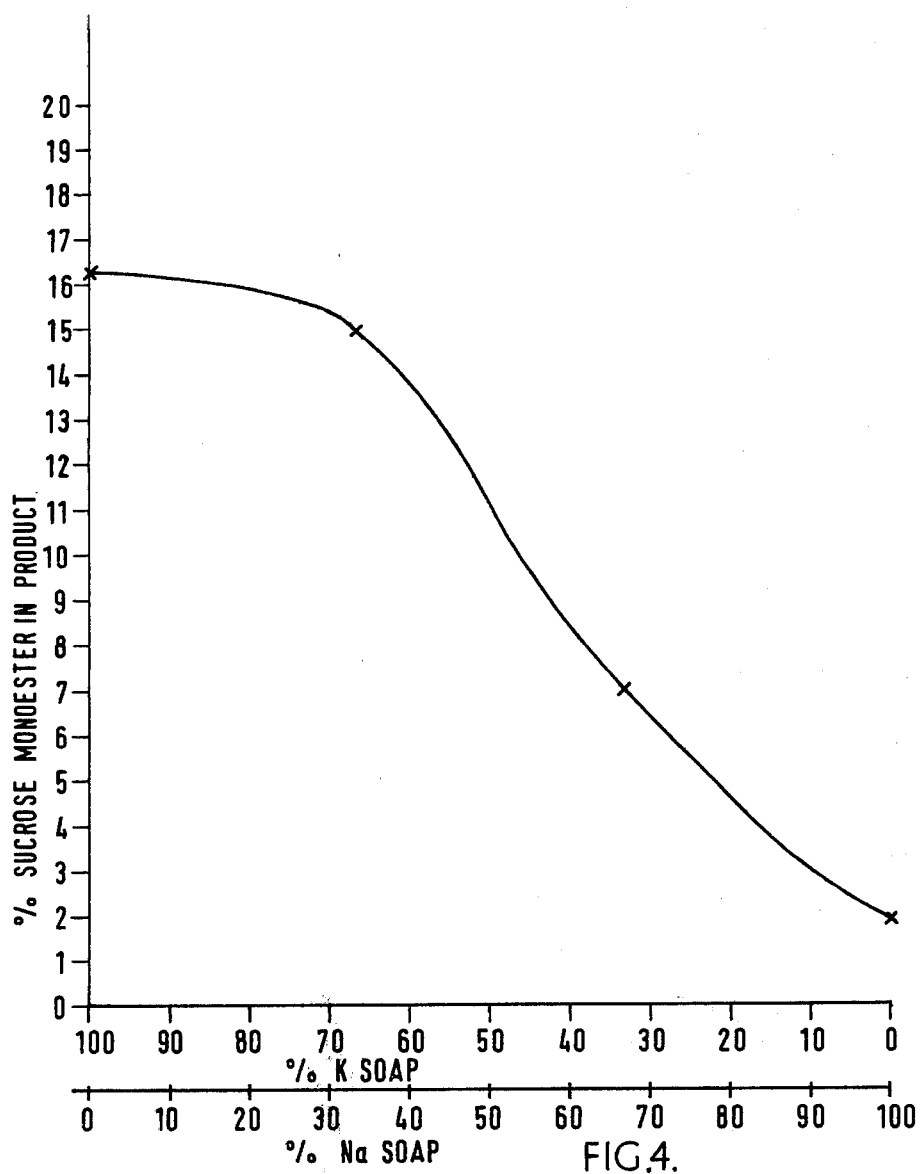
FIG. 4 represents a plot of sucrose ester level against initial soap content.

FIG. 4 shows a plot of sucrose monoester content against soap constitution and shows clearly that potassium soap is essential for the rapid and effective production of sucrose esters. It will be seen that a mixture of soaps containing up to about 50% of sodium soaps is acceptable, but sodium soap levels much above 50% give dramatically decreased yield.

EXAMPLE 4

Effect of varying hydroxyl number of feedstock

A mixture of tripalmitin, dipalmitin and monopalmitin was made by the inter-esterification of tripalmitin (300 g) with glycerol (100 g) in DMF (2liters) and in the presence of potassium carbonate (1.0 g) as catalyst at 90° C. for 12 hours. The mixture was poured into 7.5 liters of ice/water and the precipitate was filtered off and dried. The product was found to have a hydroxyl value of 150 mg KOH/g, i.e. 15,000 mg KOH/100 g.

Reaction mixtures were made up as follows:
30 g powdered sucrose (icing sugar)
30 g powdered potassium stearate
2 g powdered potassium carbonate 38 g glycerides The glycerides were made up by mixing palmitins of the desired hydroxyl value and tripalmitin. Thus, for example, for a reaction commencing with a hydroxyl value of 1500/100 g the mixture consisted of:
30 g sucrose
30 g potassium stearate
10 g mixed palmitins (OH value 150/g)
28 g tripalmitin After these ingredients had been stirred to give a homogeneous mass at 125° C., potassium carbonate (2 g) was added and the reaction commenced. The reactions were conducted under dry nitrogen to exclude possible interference by atmospheric moisture. Samples were taken at least hourly.

Figure 5:
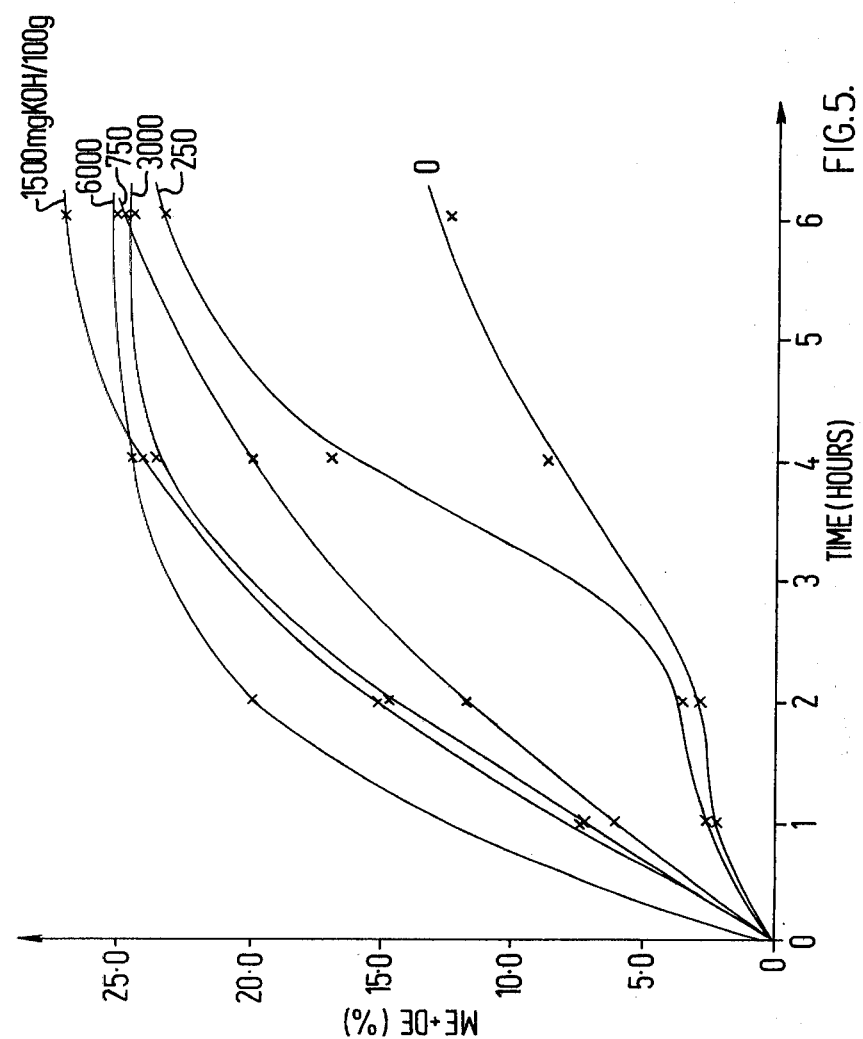
Figure 6:
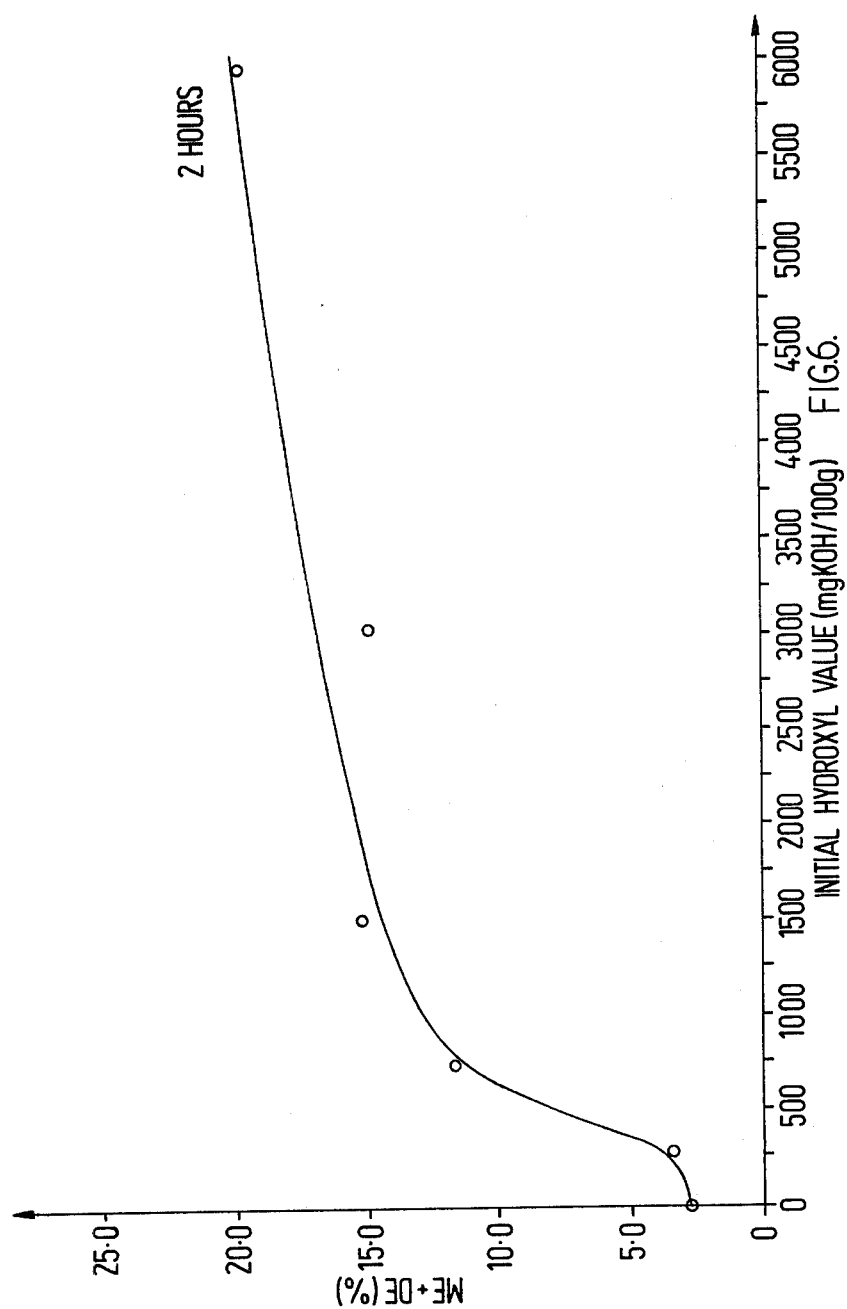
FIG. 6 represents a plot of sucrose ester level against initial hydroxyl value.

The samples were analysed for sucrose esters by GLC and the results are plotted in FIG. 5, while in FIG. 6 the ME+DE values at 2 hours are plotted against initial hydroxyl value.

It will be seen that the rate of sucrose ester production is higher in the early stages, the higher the hydroxyl value used, but the equilibrium value obtained is effectively constant above a hydroxyl value of 250. After 6 hours, the mixtures with commencing values of 750 or more have essentially reached completion (equilibrium) at 24-26% sucrose monoester and diester whereas the experiment commencing with zero hydroxyl value has reached only about 12.5%.

One of the major advantages of using the 'high soap' method is that the 'induction' period—that initial period when the apparent rate of reaction is low—is eliminated. The other period when the rate of sucrose ester production is low is towards equilibrium -i.e. in the final stages of the process. This is a consequence of the type of reaction employed and the reaction medium.

In practice, however, the cost of the time taken to increase the yield over the final period will be balanced against the value of that small amount of extra yield. Thus, referring to FIG. 5, it will be seen that if one is satisfied with 20% sucrose monoester plus diester in the product, then this can be achieved in about 3 hours if an initial OH value of 1500 or more is used. This represents a saving of 3 hours ($\frac{1}{2}$ of reaction time) for the cost of a few % sucrose ester.

It should be noted that there is little advantage in using a hydroxyl value in excess of 6000 since there is little or no further rate improvement.

EXAMPLE 5

Effect of varying hydroxyl value of feedstock

A further set of experiments was designed to demonstrate that there were advantages in a particular range of hydroxyl values where a mixture including unsaturated esters of glycerol was used and also that the desired hydroxyl value and some soap could be generated in situ. The feedstock for these experiments was made up of:

| Sucrose | 30g |
|---|---|
| Potassium carbonate | 2g |
| Tallow and potassium tallowate | 66g |
| Potassium hydroxide (85%) | see below |

The hydroxyl value was introduced by stirring tallow with proportions of soap and potassium hydroxide calculated to give 30% soap and the desired hydroxyl value in the reaction mixture. Thus, for the case with a hydroxyl value of 2000, a mixture of:

| Tallow | 47.1g |
|---|---|
| Potassium tallowate | 18.9g |
| Potassium hydroxide | 2.35g | was stirred for 1 hour at 125° C. with a vigorous purge of nitrogen gas. Sucrose (30 g) and potassium carbonate (2.0 g) were then added and reaction commenced.

Figure 7:
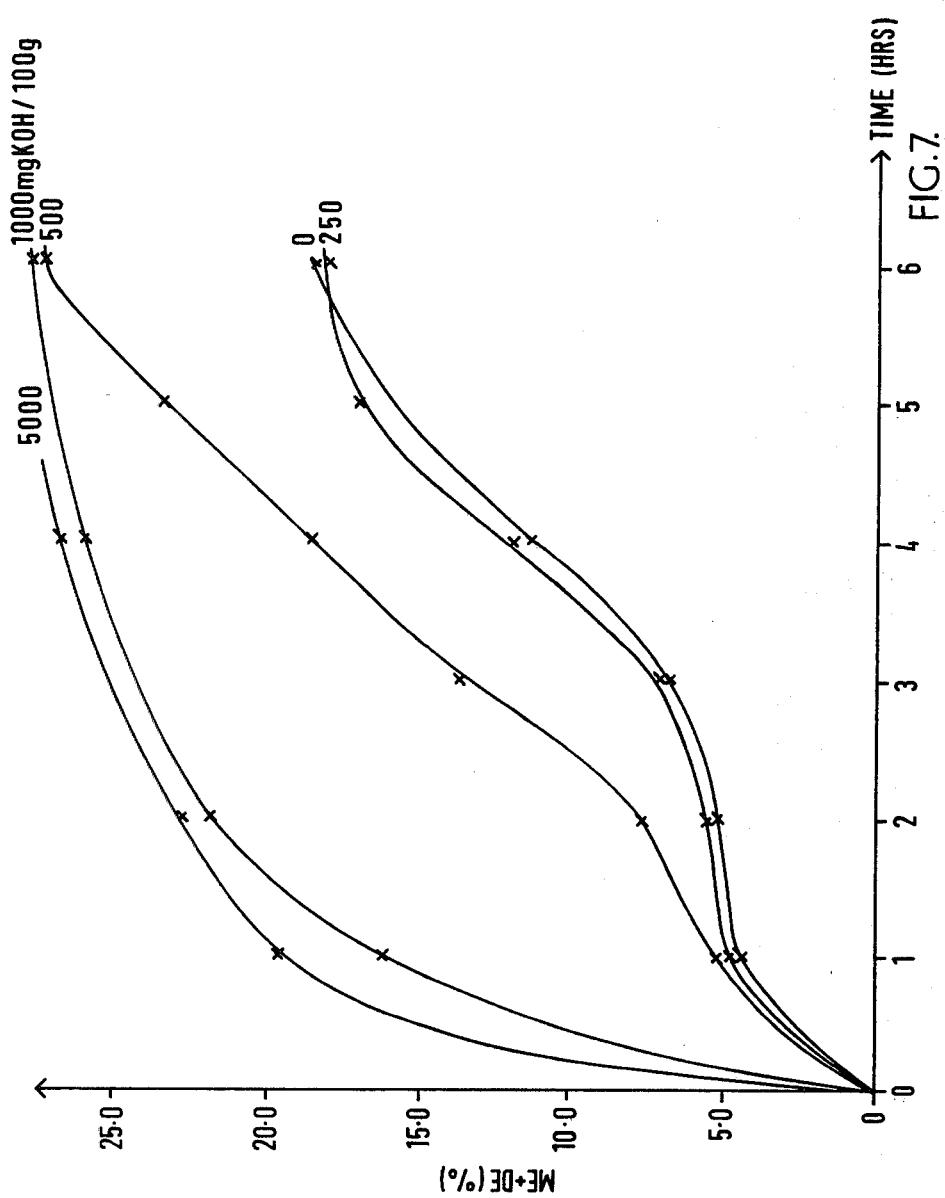

The results are plotted in FIG. 7, in a manner similar to those of Example 4 in FIG. 5. Here it is preferred to use a hydroxyl value of 1000 or more and if a product containing 20% sucrose monoester and diester is acceptable the reaction may be stopped after 1.5 hours.

EXAMPLE 6
Use of methoxide and glyceroxide as basic catalyst

Various transesterifications were effected at 125° C. using conditions as detailed in Table 3.

From Table 3, it will be seen that alkoxides lead, in general, to faster reactions than carbonate, although the sucrose ester produced in the time stated is still very much dependent on the initial soap concentration. Potassium methoxide provides a the fastest reaction of the catalystis tested, an acceptable level of sucrose monoester being obtained in as little as half an hour.

TABLE 3

| | INITIAL COMPOSITION | | | | PRODUCT | | |
|---|---|---|---|---|---|---|---|
| Glyceride (%) | Hydroxyl value of glyceride mg KOH per 100g total mixture | Sucrose (%) | Soap (%) | Catalyst (%) | Catalyst type | Time Analysed (hours) | %age Monoester |
| 38 (P)[1] | 1500 | 30 | 30 (OL)[2] | 2 | $K_2CO_3$ | 4 | 9.4 |
| | | | | | | 6 | 19.0 |
| 38 (P) | 1500 | 30 | 30 (OL) | 2 | KOMe | 4 | 18.3 |
| 38 (P) | 1500 | 30 | 30 (OL) | 2 | KO t. Bu | 4 | 18.0 |
| 38 (P) | 250 | 30 | 30 (OL) | 2 | $K_2CO_3$ | 6 | 15.6 |
| 54.5 (T)[3] | 1740 | 28.9 | 11 | 4.9 | $K_2CO_3$ | 2 | 5.0 |
| 54.5 | 3032 | 28.9 | 11 | 3.9 + 1 | $K_2CO_3$ + KOG[5] | 2 | 8.0 |
| 40 (T) | 646[4] | 27.5 | 30 (T) | 2 + ½ | $K_2CO_3$ + KOG[5] | 2 | 14.6 |
| 40 (T) | 2585[4] | 28 | 30 (T) | 2 | KOG[5] | 2 | 14.0 |
| 48 (P) | 3148 | 30.5 | 20 (P) | 1.4 | KOMe | ½ | 17.1 |
| | | | | | | 1 | 18.2 |
| 44.6 (P) | 3000 | 28.3 | 26 (P) | 1.3 | KOMe | ½ | 17.5 |
| | | | | | | 1 | 19.0 |
| 44.6 (P) | 750 | 28.4 | 26 (P) | 1.3 | KOMe | 1 | 14.1 |
| | | | | | | 2 | 17.5 |
| 39 (P) | 662 | 24.8 | 35 (P) | 1.1 | KOMe | ½ | 18.5 |
| | | | | | | 1 | 19.0 |

[1] P = Palmitate;
[2] OL = Oleate;
[3] T = Tallow;
[4] OH value from catalyst
[5] KOG = Potassium glyceroxide

EXAMPLE 7
Effect of temperature on reaction rate

A series of reactions with a feedstock of tallow (38%, of hydroxyl value 500 mgKOH/100 g of total reactants), potassium tallowate (30%), sucrose (30%) and potassium carbonate (2%) was conducted under nitrogen to examine the effect of temperature on reaction rate. The mixtures were sampled every half hour or one hour and the results are shown in Table 4 below. Analysis A is of a sample shortly before the attainment of equilibrium; analysis B represents the equilibrium concentration (except in the reaction effected at 105° C.).

TABLE 4

| Temperature | Analysis "A" | | Analysis "B" | |
|---|---|---|---|---|
| (°C.) | Time (h) | ME (%) | Time (h) | ME (%) |
| 145 | 1.5 | 16 | 2 | 18 |
| 135 | 1.5 | 17 | 2.5 | 16 |
| 125 | 3 | 12 | 4 | 18 |
| 115 | 4 | 14 | 6 | 18 |
| 105 | 8 | Inhomogenous | 16 | 15 |

As will be seen, all the reactions, with the exception of that effected at 105° C., gave a reasonable yield in a few hours. Although the equilibrium time at 145° C. was only two hours, the colour formation at this temperature was significantly worse than 135° C. and thus the preferred operating temperature is between 120° and 135° C.

One particularly important feature of the present invention is that, as indicated above, a reasonable yield can be obtained in a short time. Reference to the plots of sucrose ester content against time, e.g. FIGS. 1 and 5, shows that the shape of the curve includes an initial steep rise followed by a slow rise to equilibrium. This means that some 75% of the eventual equilibrium yield of sucrose esters is obtained in far less than 75% of the equilibrium time. In general, it is possible, especially at initial soap levels of 20% or more, to terminate the reaction after at most one half of the time taken to reach equilibrium. In fact, the reaction can advantageously be terminated after about one third of the equilibrium. What that time is will of course depend on the amount of soap initially present, the hydroxyl value of the starting mixture and on the reaction temperature (as explained in this Example).

Using 20-30% by weight of soap and a hydroxyl value of 1000 to 7500 mg KOH/100 g, a maximum of 3 hours is adequate for a reasonable yield at the lower end of the temperature range, while 2 hours maximum is sufficient at the upper end. Under the most favourable conditions, at about 120°-130° C. the reaction time may be as short as 1.5 hours or even less. Thus in FIG. 1 it can be seen that an initial soap of 30%, after only 1 hour the ME+DE yield is about 23%, while the equilibrium yield reached in, say, 4 hours is about 28%. Thus in a quarter of the equilibrium time about 82% of the equilibrium yield can be obtained.

However, it will be understood that before equilibrium is reached, the mixture will contain less sucrose ester and probably less soap, but more glycerides, than the equilibrium mixture. The foaming characteristics are significantly influenced by the soap:sucrose ester:-glyceride balance and we find that for high foaming products it is necessary to keep the glyceride content of the product as low as possible. This is conveniently achieved by prolonging the reaction time to approach equilibrium. Other ways of controlling the glyceride content are explained below in the following Examples.

EXAMPLE 8

Effect of initial composition on product composition and HLB value

A series of reactions was effected using differing starting mixtures, each with potassium carbonate as catalyst at 125° C. The results are summarised in Table 5 below.

TABLE 5

| | RUN NUMBER | | | | | |
|---|---|---|---|---|---|---|
| | 1 | 2 | 3 | 4 | 5 | 6 |
| INITIAL COMPOSITION | | | | | | |
| OH value | 3074 | 3074 | 5000 | 1500 | 3000 | 1500 |
| glyceride % | 47 | 41 | 38 | 38 | 23 | 23 |
| sucrose % | 29 | 35 | 30 | 30 | 45 | 45 |
| soap % | 17 | 17 | 30 | 30 | 30 | 30 |
| reaction time (h) | >8 | >8 | 4 | 6 | 2 | 4 |
| Product Composition | | | | | | |
| soap % | 28 | 29 | 41 | 43 | 36 | 36 |
| monoester % | 16 | 15 | 18 | 18 | 17 | 18 |
| diester % | 8 | 7 | 7 | 8 | 6 | 7 |
| sucrose % | 14 | 22 | 15 | 14 | 30 | 33 |
| monoglyceride % | 13 | 13 | 11 | 8 | 7 | 4 |
| diglyceride % | 17 | 11 | 6 | 5 | 3 | 2 |
| triglyceride % | 4 | 3 | 2 | 4 | 0.4 | 0 |
| HLB | 10-11 | 12 | 14 | 14-15 | 15 | 15+ |

Key:
1 Pilot plant run; tallow
2 Pilot plant run; tallow
3 Laboratory scale; tallow
4 Laboratory scale; tripalmitin
5 Laboratory scale; tallow
6 Laboratory scale; tripalmitin.

Run No. 5 was effected by mixing tallow (36.6 g) at 125° C. with ground potassium hydroxide (3.5 g, 85% purity) and forming potassium soap in situ. Ground sucrose (45 g) and potassium carbonate (2.0 g) were added to the stirred mixture and samples were analysed at half hourly intervals thereafter. The other Runs were effected by adding potassium carbonate (2%) to the other ingredients mixed at 125° C. and sampling at hourly intervals. In each case the reaction was continued until it approached equilibrium (i.e. the rise in sucrose ester content approached zero).

It will be seen that as the initial soap level is increased from 17 to 30% (i.e. Runs 1 and 2 compared with Runs 3 and 4) and as the initial sucrose level is increased from 30 to 45% (i.e. Runs 3 and 4 compared with Runs 5 and 6) with HLB value of the product is increased.

EXAMPLE 9

Effect of recirculation and sucrose levels

A 2000 liter reactor was fitted with a paddle stirrer rated 2 KW (2.67 h.p.). The stirrer was fitted with two impeller units, each consisting of four blades inclined at 45°. The overall diameter of each unit was 762 mm with a blade width of 162 mm. The surface area of each unit was 0.22 m². The reactor was also fitted with means for providing a captive nitrogen atmosphere. From the bottom of the reactor extended an external recirculation loop, serving to extract molten reactants and return them to the top of the reactor via a centrifugal pump. The loop was formed in two parts: a suction line, formed of 72 mm internal diameter pipe including one 90° elbow, a control valve, and an enlarger to increase the diameter to 144 mm; and a discharge line formed of 144 mm diameter pipe including an open valve, two 90° elbows, two 45° elbows and a T-junction; the two parts being separated by a 144 mm diameter input and outlet centrifugal pump rated at about 10 KW. In this apparatus it was found that the initial recirculation pump speed was about 675 rev/min giving a recirculation time of about 0.56 min. The reaction was effected by charging the reactor with tallow under a nitrogen atmosphere, heating it to about 125° C. and gradually adding KOH over one hour so that the triglyceride was converted in part into some diglyceride and some soap, possibly together with a certain amount of monoglyceride. The completion of the KOH addition is regarded as time zero for the following operations. After one hour the K₂CO₃ and sucrose addition was started and was completed after three hours. After about two hours the recirculation pump became torque-limited and the speed began to drop, reaching a minimum of 60 rev/min after six hours, equivalent in a recirculation time of 8.85 min. The reduction in speed over four hours was approximately linear.

The reaction was continued for a further twelve hours, making a total of eighteen hours. The total number of circulations of the reaction mix during this time was calculated at about 460.

This procedure was carried out in seven runs, 1-3 being outside the scope of the present invention and 4-7 inside. Each reaction had reached equilibrium and thus the comparison is of equilibrium results and not results after a shorter, but optional, time.

The starting mixture comprised 10 to 40% by weight of sucrose as in Table 6.

TABLE 6

| RUN NO. | % BY WEIGHT OF REACTANTS | | | | INITIAL SOAP (%) |
|---|---|---|---|---|---|
| | TALLOW | KOH | $K_2CO_3$ | SUCROSE | |
| 1 | 83.4 | 1.75 | 4.85 | 10.0 | 11.96 |
| 2 | 78.4 | 1.75 | 4.85 | 15.0 | 10.06 |
| 3 | 73.4 | 1.75 | 4.85 | 20.0 | 10.06 |
| 4 | 68.4 | 1.75 | 4.85 | 25.0 | 10.06 |
| 5 | 63.4 | 1.75 | 4.85 | 30.0 | 10.06 |
| 6 | 58.4 | 1.75 | 4.85 | 35.0 | 10.06 |
| 7 | 53.4 | 1.75 | 4.85 | 40.0 | 10.06 |

Figure 8:
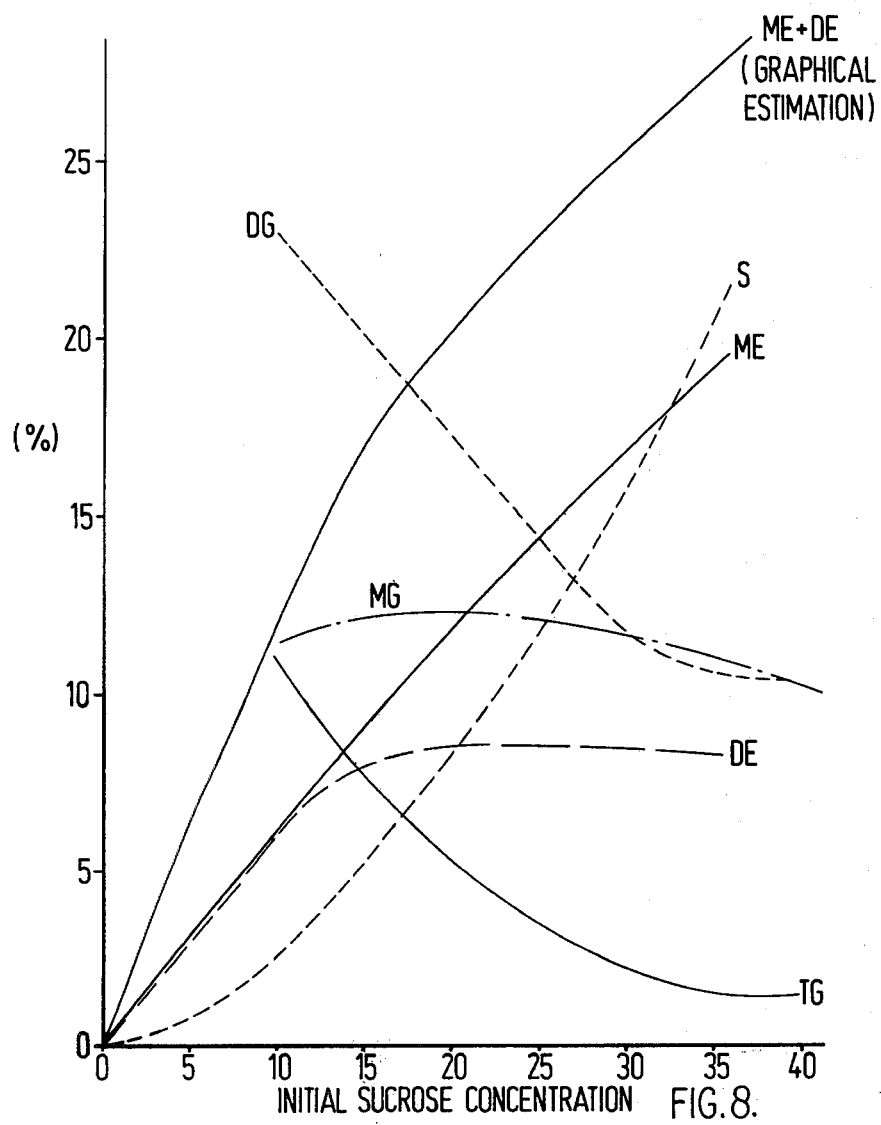
FIG. 8 represents a plot of reaction component against initial sucrose concentration.

The results obtained are shown in the accompanying FIG. 8 which shows the effect of varying the sugar concentration in the initial mixture, on the concentrations in the product of sucrose monoester (ME), sucrose diester (DE), sucrose (S), monoglyceride (MG), diglyceride (DG) and triglyceride (TG). As will be readily seen, as the sucrose level in the starting material is increased above about 20%, the level of monoester in the product is increased while the levels of monoglyceride and diester remain substantially constant.

Figure 9:
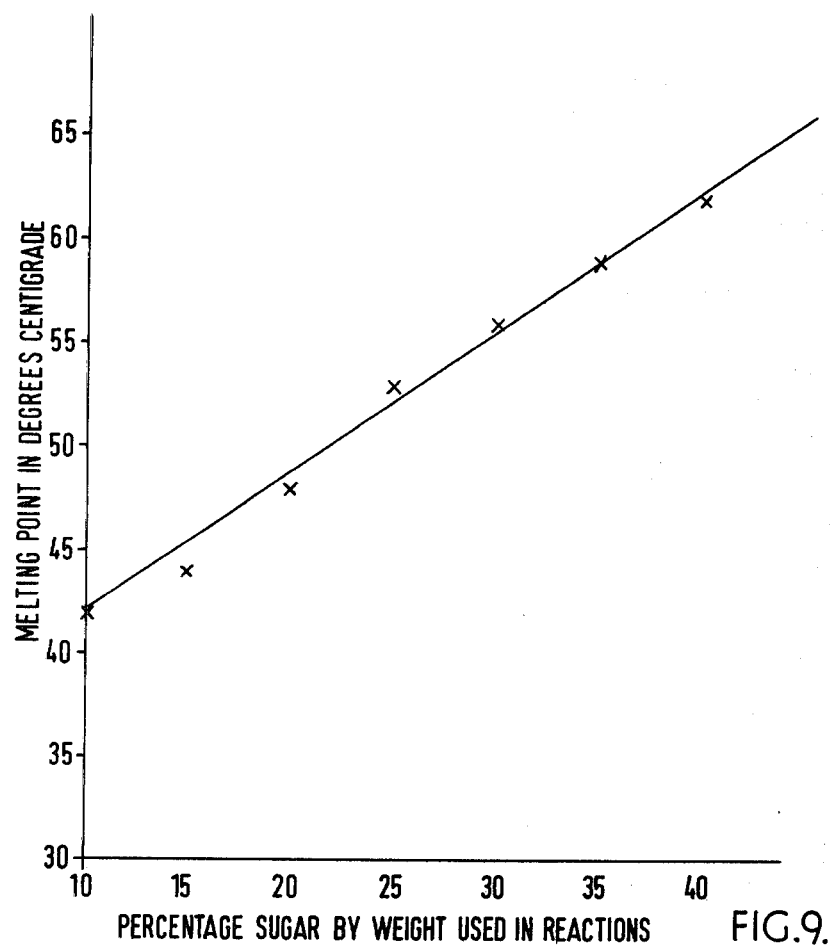
FIG. 9 represents a plot of product melting point against initial sucrose concentration.
Figure 10:
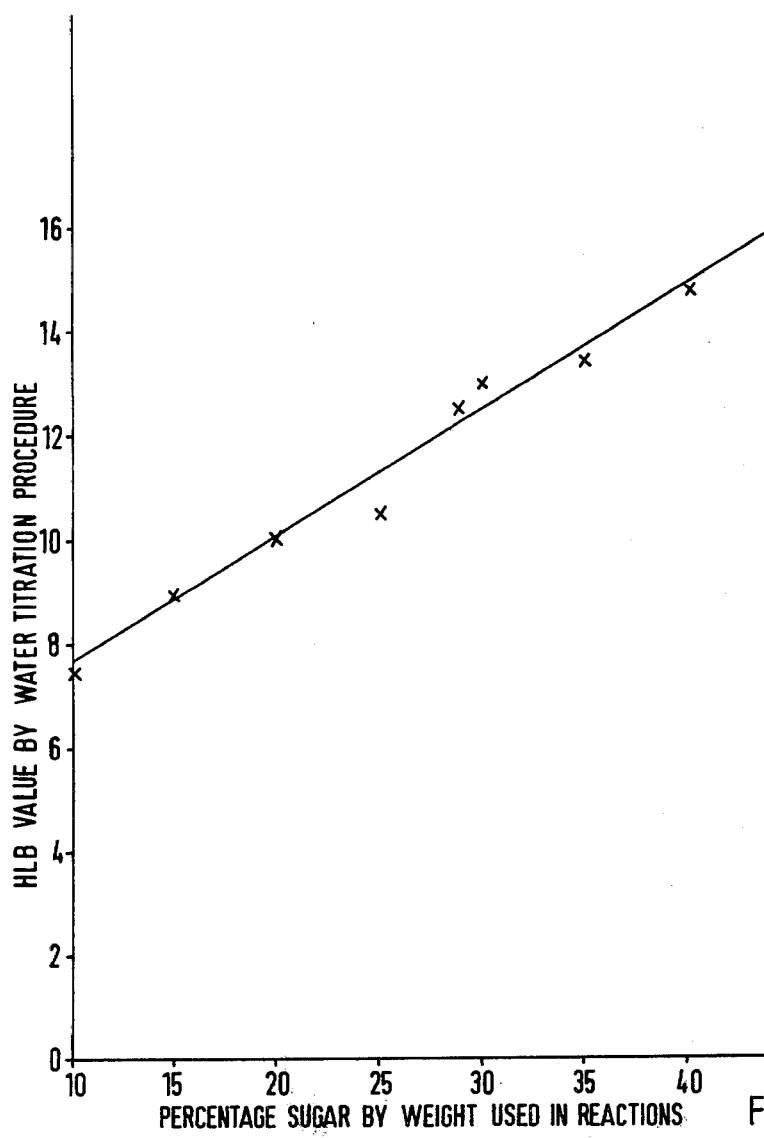
FIG. 10 represents a plot of product HLB value against initial sucrose concentration.

FIGS. 9 and 10 show the effect of initial sucrose concentration on the melting point and H.L.B. value of the product. In each case a steady rise with increasing initial sucrose concentration is seen.

In a modification of the above-described apparatus, the recirculation loop led out of the vessel through a central port in the bottom and re-entered upwards through the bottom in an eccentric position. The end of the re-entering pipe was deflected obliquely so as to divert the emerging mixture into a tangential direction of flow.

EXAMPLE 10

Semi-continuous transesterification

A stock mixture of tallow (3.96 kg), glycerol monooleate (245 g) and potassium oleate (3.0 kg) was obtained by vigorous stirring of the ingredients at 100° C.

A laboratory-scale reaction vessel was constructed from a stainless steel beaker fitted with a stirrer and a stainless steel tube leading from the base of the beaker up to a level corresponding with the desired level of the reactants in the beaker. The volume taken up by the reactants in the stirred vessel was 786 ml and the volume of the tube was 331 ml. The whole apparatus was heated in an oil bath at 130° C.

The reactor was charged with product from a batch process and heated to 125° C. About 400 g of product was then discharged from the outflow tube by suction and then 290 g of the glyceride mixture (heated to 125° C.) and 107 g of sucrose were simultaneously added to the stirred vessel. After 15 minutes, 6 g of potassium methoxide was added and after a further 15 minutes further reactants were added and the product simultaneously removed as before. Again, 6 g of potassium methoxide was added 15 minutes after the discharge and charge operation and so on. In this way 3.6 kg of the product containing an average of 12% sucrose monotallowate was obtained in 4.5 hours. This represents a throughput of about 0.8 reactor volumes per hour, working in what amounts to a semi-continuous procedure. True continuity would be achieved by gradual addition of the feedstocks and removal of the product formed.

We claim:

1. In the process for the preparation of a surfactant mixture containing sucrose mono- and di-esters, by reacting a starting mixture including solid particulate sucrose, at least one triglyceride of a fatty acid having at least 8 carbon atoms and a basic transesterification catalyst, at a temperature of from 110° to 140° C. at atmospheric pressure and in the absence of any solvent, the improvement which comprises that the starting mixture:

(a) contains a di- and/or mono-glyceride in an amount to provide a hydroxyl value of greater than 500 mg KOH/100 g of starting mixture;

(b) contains at least 10% by weight of a fatty acid soap in addition to the basic transesterification catalyst, at least 50% by weight of the soap being potassium soap, and (c) (when the soap content is less than 20% by weight) contains at least 25% by weight of sucrose.

2. A process according to claim 1, in which the soap content of the starting mixture is at least 15% by weight.

3. A process according to claim 1, in which the soap content of the starting mixture is at least 20% by weight.

4. A process according to claim 1, in which the soap content of the starting mixture is 25–30% by weight.

5. A process according to claim 1, in which the said soap comprises at least 70% by weight of potassium soap.

6. A process according to claim 1, in which the soap is added pre-formed to the starting mixture.

7. A process according to claim 6, in which the fatty acid moiety of the soap is different from that of the glycerides.

8. A process according to claim 1, in which the soap is formed in situ in the starting mixture before the addition of the sucrose.

9. A process according to claim 1, in which the basic transesterification catalyst is potassium carbonate and the hydroxyl value of the starting mixture is from 1000 to 7,500 mg KOH/100 g.

10. A process according to claim 9, in which the hydroxyl value of the starting mixture is from 1500 to 5000 mg KOH/100 g.

11. A process according to claim 1, in which the reaction mixture is mixed by recirculation.

12. A process according to claim 11, in which the recirculation is effected by use of an external recirculation loop of pipework fitted with a recirculation pump.

13. A process according to claim 1, effected in a continuous mode by continuously introducing into a reactor a glyceride and soap premix, sucrose and catalyst, mixing the so-formed reaction mixture while it is in the reactor and continuously withdrawing reacted material from the reactor.

14. A process according to claim 1, in which the sucrose content of the starting mixture is from 27.5 to 40% by weight.

15. A process for the preparation of a surfactant mixture containing sucrose mono- and diesters, by reacting a starting mixture including solid particulate sucrose, at least one triglyceride of a fatty acid having at least 8 carbon atoms and a basic transesterification catalyst, at a temperature of from 100° to 140° C. at atmospheric pressure and in the absence of any solvent, wherein the starting mixture:

(a) contains a di- and/or mono-glyceride in an amount to provide a hydroxyl value of between about 1000 and about 7500 mg KOH/100 g of starting mixture;

(b) contains 20 to 30% by weight of a fatty acid soap in addition to the basic transesterification catalyst, at least 70% by weight of the soap being potassium soap, and (c) contains 27.5–40% by weight of sucrose.

16. A process according to claim 15, in which the reaction is terminated after at most one half of the time taken to reach equilibrium under the the conditions used.

17. A process according to claim 15, in which the reaction is terminated after at most one third of the time taken to reach equilibrium under the conditions used.

18. A process according to claim 15, effected at a temperature of from 110° to 125° C. for a maximum of 3 hours.

19. A process according to claim 15, effected at a temperature of from 125° to 140° C. for a maximum of 2 hours.

20. A process according to claim 15, effected at a temperature of from 120° to 130° C. for a maximum of 1.5 hours.

* * * * *